US010932664B2

(12) United States Patent
Hirose et al.

(10) Patent No.: US 10,932,664 B2
(45) Date of Patent: Mar. 2, 2021

(54) OPHTHALMIC DEVICE

(71) Applicant: TOPCON CORPORATION, Tokyo (JP)

(72) Inventors: Ryoichi Hirose, Tokyo (JP); Ikuo Ishinabe, Saitama (JP); Tatsuo Yamaguchi, Warabi (JP)

(73) Assignee: TOPCON CORPORATION, Tokyo (JP)

( * ) Notice: Subject to any disclaimer, the term of this patent is extended or adjusted under 35 U.S.C. 154(b) by 37 days.

(21) Appl. No.: 16/061,724

(22) PCT Filed: Jul. 29, 2016

(86) PCT No.: PCT/JP2016/072437
§ 371 (c)(1),
(2) Date: Jun. 13, 2018

(87) PCT Pub. No.: WO2017/104162
PCT Pub. Date: Jun. 22, 2017

(65) Prior Publication Data
US 2019/0000316 A1   Jan. 3, 2019

(30) Foreign Application Priority Data

Dec. 18, 2015   (JP) .............................. JP2015-246945

(51) Int. Cl.
*A61B 3/12*    (2006.01)
*A61B 3/10*    (2006.01)
(Continued)

(52) U.S. Cl.
CPC ................ *A61B 3/12* (2013.01); *A61B 3/102* (2013.01); *A61B 3/1025* (2013.01); *A61B 3/117* (2013.01);
(Continued)

(58) Field of Classification Search
CPC ..... A61B 3/12; A61B 3/10258; A61B 3/1173; A61B 5/0066; A61B 3/102; A61B 3/14; A61B 3/1025; A61B 3/1225; A61B 3/117
See application file for complete search history.

(56) References Cited

U.S. PATENT DOCUMENTS

| 5,815,242 A | 9/1998 | Anderson et al. |
| 2003/0103191 A1 | 6/2003 | Staurenghi et al. |

(Continued)

FOREIGN PATENT DOCUMENTS

| EP | 1308124 A2 | 5/2003 |
| JP | H11-197109 A | 7/1999 |

(Continued)

OTHER PUBLICATIONS

International Search Report and Written Opinion dated Oct. 11, 2016 in connection with International Patent Application No. PCT/JP2016/072437, 5 pgs.

(Continued)

*Primary Examiner* — Jack Dinh
(74) *Attorney, Agent, or Firm* — Chiesa Shahinian & Giantomasi PC

(57) ABSTRACT

An ophthalmic device that comprises a first objective lens system, an optical system, an anterior eye segment photographing system, and a first optical-path combining member. The first objective lens system includes two or more lenses. The optical system includes a projection system configured to project light onto a target eye via the first objective lens system. The anterior eye segment photographing system is used for photographing an anterior eye segment of the target eye. The first optical-path combining member is located between the two or more lenses to combine an optical path of the optical system and an optical path of the anterior eye segment photographing system.

16 Claims, 8 Drawing Sheets

(51) Int. Cl.
*A61B 3/14* (2006.01)
*A61B 3/117* (2006.01)
*A61B 5/00* (2006.01)

(52) U.S. Cl.
CPC .............. *A61B 3/14* (2013.01); *A61B 5/0066* (2013.01); *A61B 3/1173* (2013.01)

(56) References Cited

U.S. PATENT DOCUMENTS

| | | |
|---|---|---|
| 2009/0093798 A1 | 4/2009 | Charles |
| 2011/0176111 A1 | 7/2011 | Taki et al. |
| 2012/0092615 A1 | 4/2012 | Izatt et al. |
| 2012/0188510 A1 | 7/2012 | Suehira et al. |
| 2012/0249769 A1 | 10/2012 | Naba et al. |
| 2013/0304046 A1 | 11/2013 | Charles |
| 2014/0094784 A1 | 4/2014 | Charles |
| 2014/0094785 A1 | 4/2014 | Charles |
| 2015/0245765 A1 | 9/2015 | Fujii et al. |
| 2015/0265465 A1 | 9/2015 | Charles |
| 2017/0079844 A1 | 3/2017 | Charles |

FOREIGN PATENT DOCUMENTS

| | | |
|---|---|---|
| JP | 2006-322767 A | 11/2006 |
| JP | 2008-099716 A | 5/2008 |
| JP | 2010-197180 A | 9/2010 |
| JP | 2011501985 A | 1/2011 |
| JP | 2011-147609 A | 8/2011 |
| JP | 2012075641 A | 4/2012 |
| JP | 2012147976 A | 8/2012 |
| JP | 2012-213602 A | 11/2012 |
| JP | 2015-100512 A | 6/2015 |
| JP | 2015-160103 A | 9/2015 |
| JP | 2015198723 A | 11/2015 |

OTHER PUBLICATIONS

Notice of Reasons for Refusal dated Sep. 17, 2019, in connection with Japanese Patent Application No. 2015-246945, 15 pgs.

OPHTHALMIC DEVICE

CROSS-REFERENCE TO RELATED APPLICATIONS

This application is a national stage (under 35 U.S.C. 371) of International Patent Application No. PCT/JP2016/072437, filed Jul. 29, 2016, claiming priority to Japanese Patent Application No. 2015-246945, filed Dec. 18, 2015, both of which are herein incorporated by reference in their entirety.

FIELD

Embodiments described herein relate to an ophthalmic device.

BACKGROUND

Ophthalmic devices capable of observing or photographing an eye fundus or the like of a subject's eye easily in a wide view are required for ophthalmic devices used for screening or treatment of ophthalmic diseases. Scanning Laser Ophthalmoscopes (SLO) are known as such ophthalmic devices. The SLO scans the eye fundus with light and detects return light therefrom using a light receiving device to thereby form an image of the eye fundus.

In general, it is necessary to increase a diameter of an objective lens for observing the eye fundus etc. in a wide view using the ophthalmic device. However, increasing the diameter of the objective lens leads to increasing the cost and the size of the device. Therefore, various types of methods for observing the eye fundus etc. in a wide view while suppressing the increase of the diameter of the objective lens are suggested.

For example, EP Unexamined Patent Application Publication No. 1308124 (hereinafter the "EP Application '124") discloses a method of obtaining a wide-angle image of the subject's eye by bring a contact lens included in an objective lens system into contact with a cornea of the subject's eye. Besides, for example, U.S. Pat. No. 5,815,242 (hereinafter the "U.S. Pat. No. '242") discloses a method of photographing an anterior eye segment of the subject's eye using an anterior eye segment photographing system provided in an ophthalmic device for obtaining a wide-angle image of the subject's eye with an ellipsoidal mirror.

However, in the method disclosed in EP Application '124, the contact lens is used. Therefore, from a viewpoint of safety, it becomes difficult to perform the alignment for a position matching of an optical system with respect to the subject's eye. Thereby, this brings upon a problem of leading to lost the convenience of the ophthalmic device for user.

On the other hand, in the method disclosed in U.S. Pat. No. '242, the ophthalmic device is capable of specifying a position of the subject's eye from an image of the anterior eye segment of the subject's eye obtained by using the anterior eye segment photographing system. However, also in the method disclosed in U.S. Pat. No. '242, it is necessary to increase the size of the ellipsoidal mirror to obtain a wide-angle image of the subject's eye. This brings upon a problem of impossibility in satisfying both widening an angle of the image of the subject's eye and the downsizing of the device.

As described above, under the conventional technology, it is difficult to project light onto the subject's eye in a wide range so as to observe the eye fundus etc. of the subject's eye in a wide view while downsizing the device.

SUMMARY

An ophthalmic device of embodiments comprises a first objective lens system, an optical system, an anterior eye segment photographing system, and a first optical-path combining member. The first objective lens system includes two or more lenses. The optical system includes a projection system configured to project light onto a target eye via the first objective lens system. The anterior eye segment photographing system is used for photographing an anterior eye segment of the target eye. The first optical-path combining member is located between the two or more lenses to combine an optical path of the optical system and an optical path of the anterior eye segment photographing system.

DETAILED DESCRIPTION

Figure 1:
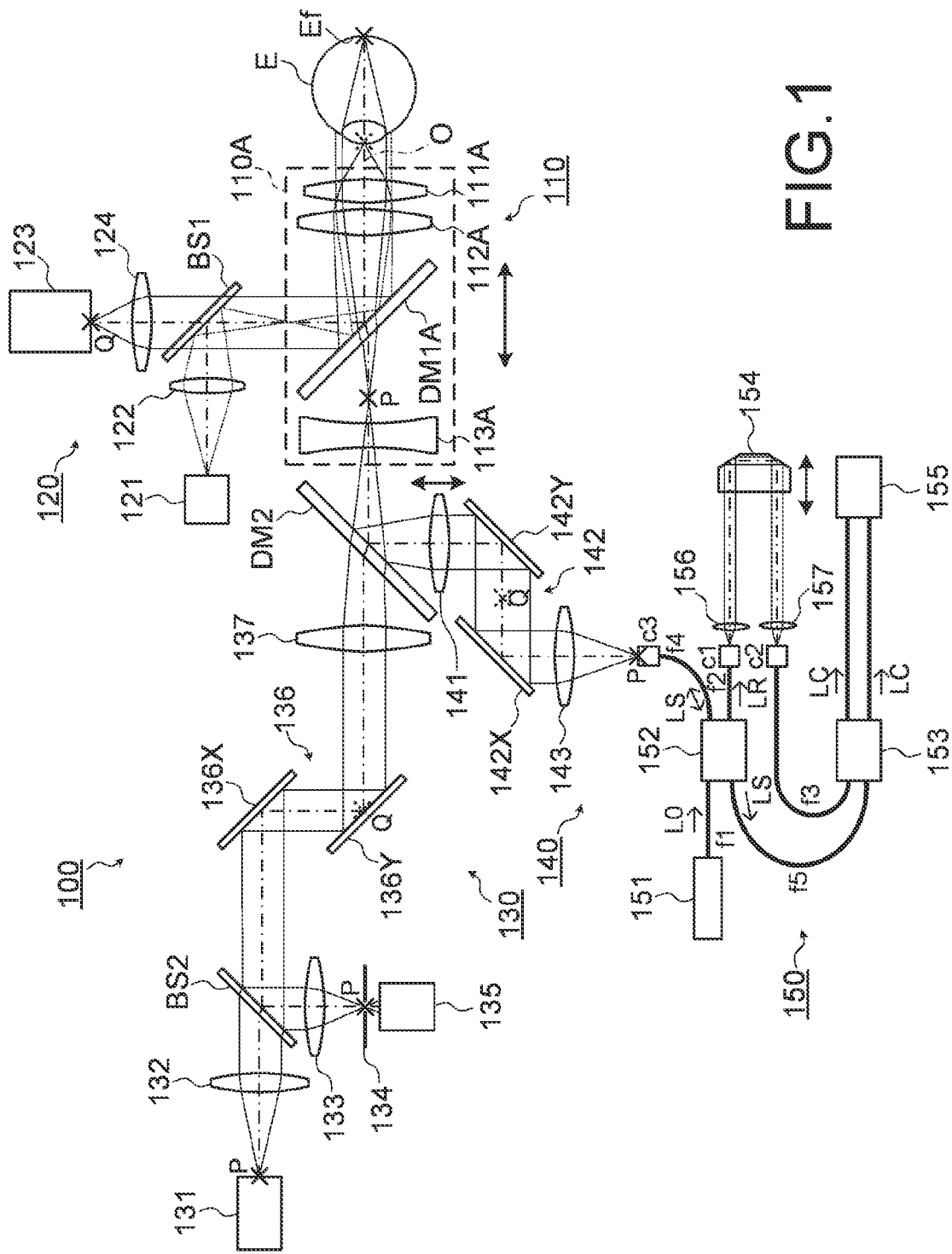
FIG. 1 is a schematic diagram illustrating an example of the configuration of an optical system of an ophthalmic device according to embodiments.

This disclosure is intended to provide an ophthalmic device capable of projecting light onto a subject's eye in a wide range while downsizing the device.]

Referring now to the drawings, exemplary embodiments of an ophthalmic device according to the present invention are described below. Any of the contents of the documents cited in the present specification and arbitrary known techniques may be applied to the embodiments below.

The ophthalmic device according to embodiments is capable of projecting light through a pupil of a subject's eye (target eye, patient's eye) onto a posterior eye segment (eye fundus, vitreous body, or the like) of the subject's eye in a wide range, by deflecting light from a light source using an optical scanner and irradiating the subject's eye with the deflected light. Such a configuration can be applied to any ophthalmic device capable of irradiating the posterior eye segment with light. Examples of such ophthalmic device capable of irradiating the posterior eye segment with light include laser treatment apparatuses for irradiating the treatment site on the eye fundus with laser light, perimeters for measuring a field of view based on responses of the subject (patient) while moving a visual target with the fixation of the subject's eye, or the like.

Besides, the ophthalmic device according to the embodiments is capable of forming distribution (image, distribution of the thickness of layer, distribution of lesion, or the like) of a predetermined data of the posterior eye segment of the subject's eye by receiving return light from the posterior eye segment of the subject's eye. Such a configuration can be applied to any ophthalmic device capable of acquiring data by scanning the posterior eye segment with light. Examples of such ophthalmic device capable of scanning the posterior eye segment with light include SLO that obtains a front image of the eye fundus by laser scanning using a confocal optical system, OCT (Optical Coherence Tomography) for acquiring a tomographic image of the eye fundus, and multifunctional products having functions of OCT and SLO combined together. In the following embodiments, the ophthalmic device is described as, for example, having functions of SLO and functions of OCT.

In some cases in the following description, the left/right direction viewed from a subject is regarded as the X direction, the up/down direction is regarded as the Y direction, and the depth direction of an optical system viewed from the subject is regarded as the Z direction.

[Optical System]

Figure 2:
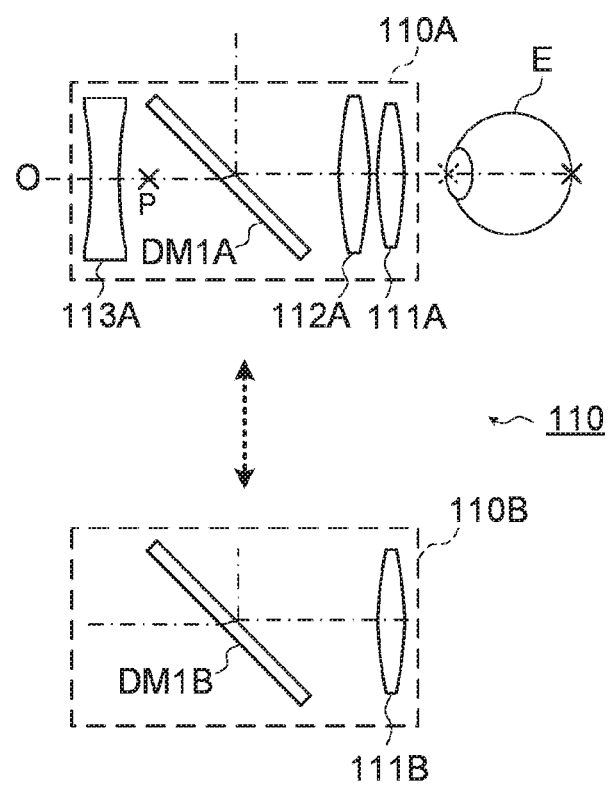
FIG. 2 is a schematic diagram illustrating an example of the configuration of an optical system of an ophthalmic device according to the embodiments.
Figure 3:
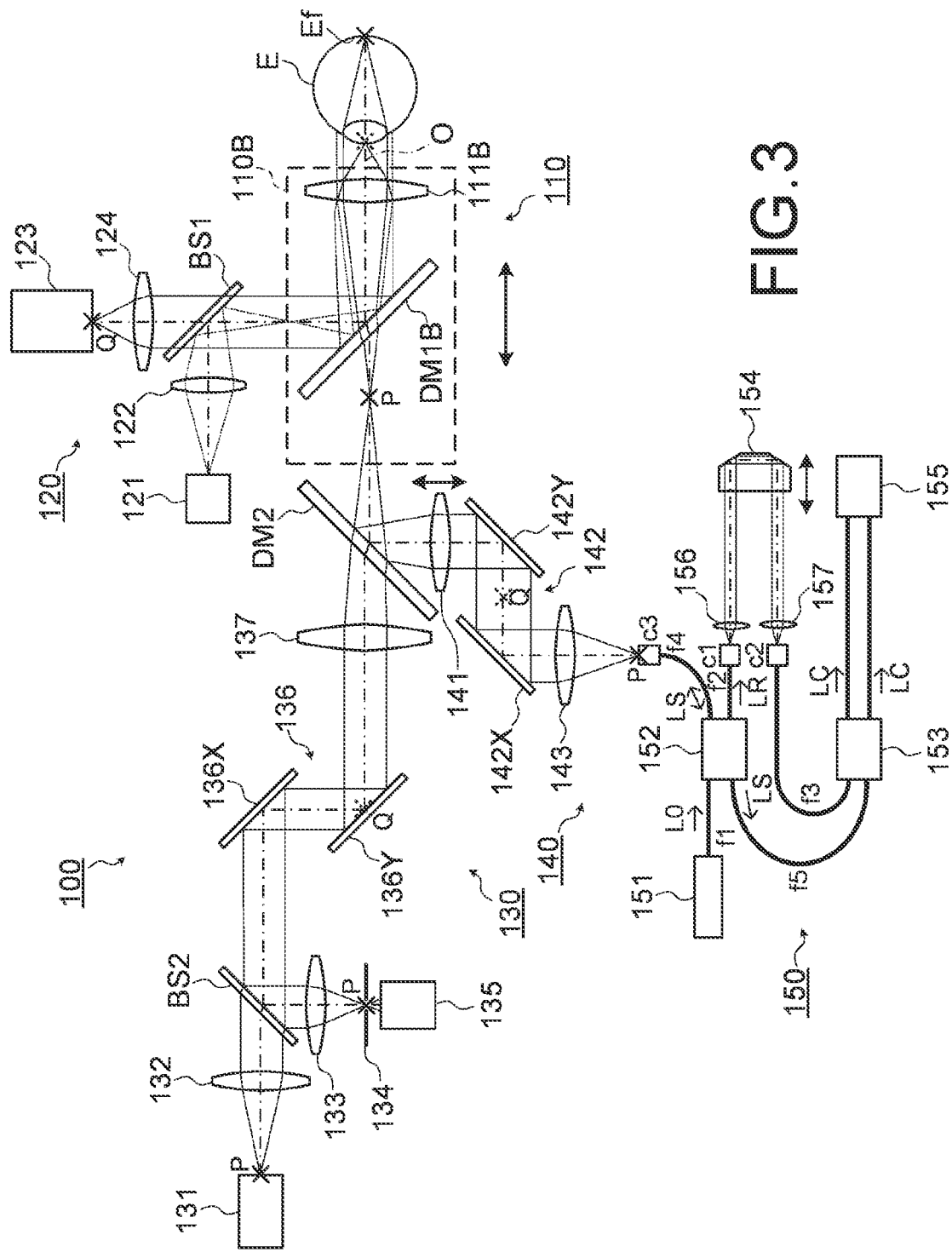
FIG. 3 is a schematic diagram illustrating an example of the configuration of an optical system of an ophthalmic device according to the embodiments.

FIGS. 1 to 3 illustrate an example of the configuration of the optical system of the ophthalmic device according to the embodiments. The ophthalmic device is capable of acquiring images of the subject's eye in various ranges corresponding to photographing modes. In the ophthalmic device, an objective lens unit corresponding to the photographing mode can be disposed in an optical axis of the optical system.

FIG. 1 illustrates an example of the configuration of the optical system of the ophthalmic device when the photographing mode is set to the wide-angle (wide angle of view) photographing mode. FIG. 2 illustrates an example of the configuration of the objective lens system according to the embodiments. The objective lens system can be switched according to the photographing mode. In FIG. 2, like reference numerals designate like parts as in FIG. 1. The same description may not be repeated. FIG. 3 illustrates an example of the configuration of the optical system of the ophthalmic device when the photographing mode is set to the high magnification photographing mode. In FIG. 3, like reference numerals designate like parts as in FIG. 1 or 2. The same description may not be repeated. In FIGS. 1 and 3, a position optically conjugate with the eye fundus Ef of the subject's eye E is illustrated as an eye fundus conjugate position P, and a position optically conjugate with the pupil of the subject's eye E is illustrated as a pupil conjugate position Q.

An optical system 100 includes a projection system that projects light onto the subject's eye via an objective lens system 110 and a light receiving system that receives return light of the light projected onto the subject's eye by the projection system via the objective lens system 110. The ophthalmic device forms an image based on a light receiving result obtained by the light receiving system. The ophthalmic device according to the embodiments can form an SLO image and an OCT image. That is, the optical system 100 includes an SLO optical system 130 and an OCT optical system 140. The SLO optical system 130 includes an SLO projection system and an SLO light receiving system. The OCT optical system 140 includes an OCT projection system and an OCT light receiving system.

The ophthalmic device is provided with an anterior eye segment photographing system (an anterior eye segment observing system) 120 for photographing the anterior eye segment of the subject's eye. The optical system 100 is movable with the objective lens system 110 and the anterior eye segment photographing system 120 in the X direction, the Y direction, and the Z direction by means of a moving mechanism (not illustrated, a moving mechanism 100D to be hereinafter described). The moving mechanism moves the optical system 100 etc. based on image(s) of the anterior eye segment of the subject's eye E, thereby the ophthalmic device can perform the alignment for the position matching of the optical system 100 with respect to the subject's eye E. Hereinafter, cases in which the optical system 100 includes the objective lens system 110 and the anterior eye segment photographing system 120 will be described. However, the optical system 100 may not include these systems.

(Objective Lens System)

In the ophthalmic device, an objective lens unit corresponding to the photographing mode can be disposed in an optical axis O of the optical system 100. In the embodiments, the photographing modes include a wide-angle photographing mode for photographing the subject's eye E with a first range (e.g., the angle of view of 100 degrees) and a high magnification photographing mode for photographing the subject's eye E with a second range (e.g., the angle of view of 50 degrees) which is narrower than the first range.

The objective lens system 110 includes an objective lens unit 110A and an objective lens unit 110B (see FIG. 2). For example, the objective lens units 110A and 110B can be disposed selectively in the optical axis O manually by a publicly known rotation mechanism or slide mechanism. In the wide-angle photographing mode, the objective lens unit 110A is disposed so that an optical axis of the objective lens unit 110A coincides with the optical axis of the optical system 100 (FIG. 1). In the high magnification photographing mode, the objective lens unit 110B is disposed so that an optical axis of the objective lens unit 110B coincides with the optical axis O (FIG. 3).

The objective lens unit 110A includes two or more lenses. A dichroic mirror DM1A is arranged between the two or more lenses. For example, the objective lens unit 110A may be a lens unit (Nagler type) including convex lenses 111A and 112A and a concave lens 113A. The convex lens 111A, the convex lens 112A and the concave lens 113A are arranged in this order from the subject's eye E. Between the convex lens 112A and the concave lens 113A, the dichroic mirror DM1A is disposed. In the wide-angle photographing mode, the dichroic mirror DM1A is an optical-path combining member to combine an optical path of the anterior eye segment photographing system 120 and both of an optical path of the SLO optical system 130 and an optical path of the OCT optical system 140. The position (the eye fundus conjugate position) P which is optically conjugate with the eye fundus (retina) of the subject's eye E or in the vicinity of the position is arranged between the dichroic mirror DM1A and the concave lens 113A. The objective lens unit 110A may include the dichroic mirror DM1A.

The dichroic mirror DM1A transmits light (SLO light) from the SLO optical system 130, return light of the SLO light from the subject's eye E, light (OCT light, measurement light) from the OCT optical system 140, and return light of the OCT light from the subject's eye E. The dichroic mirror DM1A reflects light from the anterior eye segment photographing system 120 toward the subject's eye E, and reflects return light from the subject's eye E toward the anterior eye segment photographing system 120, the return light being return light of the light from the anterior eye segment photographing system 120.

The objective lens unit 110B includes at least one lens. A dichroic mirror DM1B is arranged on light sources (an SLO light source and an OCT light source) side with respect to the at least one lens. For example, the objective lens unit 110B may include a convex lens 111B. In the high magnification photographing mode, the dichroic mirror DM1B is an optical-path combining member to combine an optical path of the anterior eye segment photographing system 120 and both of the optical path of the SLO optical system 130 and the optical path of the OCT optical system 140. The objective lens unit 110B may include the dichroic mirror DM1B.

In the same manner as the dichroic mirror DM1A, the dichroic mirror DM1B transmits light (SLO light) from the SLO optical system 130, return light of the SLO light from the subject's eye E, light (OCT light, measurement light) from the OCT optical system 140, and return light of the OCT light from the subject's eye E. Besides, the dichroic mirror DM1B reflects light from the anterior eye segment photographing system 120 toward the subject's eye E, and reflects return light from the subject's eye E toward the anterior eye segment photographing system 120, the return light being return light of the light from the anterior eye segment photographing system 120. A position of the dichroic mirror DM1B on the optical axis O when the objective lens unit 110B is disposed in the optical axis O may be substantially the same as a position of the dichroic mirror DM1A when the objective lens unit 110A is disposed in the optical axis O. This eliminates the need for adjustment of a position or an orientation of the anterior eye segment photographing system 120 when the photographing mode is changed.

The objective lens unit 110A may merely include the convex lens 111A, the convex lens 112A, and the concave lens 113A, and the objective lens unit 110B may merely include the convex lens 111B. Thereby, the dichroic mirrors DM1A and DM1B can be shared by one dichroic mirror when the objective lens unit disposed in the optical axis O is switched.

The objective lens system 110 is movable along the optical axis O by means of a moving mechanism (not illustrated, a moving mechanism 110D to be hereinafter described). As a result, it is possible to move the objective lens system 110 with respect to the optical system 100 in the Z direction. Therefore, both of a focus position of the SLO optical system 130 and a focus position of the OCT optical system 140 can be changed.

Hereinafter, a case is mainly described in which the objective lens unit 110A is disposed in the optical axis O.

(Anterior Ocular Segment Photographing System)

The anterior eye segment photographing system 120 includes an anterior eye segment illumination light source 121, a collimator lens 122, an anterior eye segment photographing camera 123, an imaging lens 124, and a beam splitter BS1. The beam splitter BS1 is an optical-path combining member to combine an optical path of the return light of illumination light for illuminating the anterior eye segment of the subject's eye E and an optical path of the illumination light.

The anterior eye segment illumination light source 121 is a light source for illuminating the anterior eye segment of the subject's eye E. The anterior eye segment photographing camera 123 includes an imaging device to detect reflection light (return light) from the anterior eye segment of the subject's eye E illuminated by the anterior eye segment illumination light source 121. An LED emitting light having a center wavelength of 950 nm is used as the anterior eye segment illumination light source 121, for example. Light emitted from the anterior eye segment illumination light source 121 is collimated into a parallel light flux by a collimator lens 122. The illumination light collimated into the parallel light flux is reflected toward the dichroic mirror DM1A by the beam splitter BS1. The illumination light reflected by the beam splitter BS1 is deflected toward the subject's eye E by the dichroic mirror DM1A. The return light of the illumination light from the subject's eye E is reflected by the dichroic mirror DM1A, and the reflected return light penetrates the beam splitter BS1. The return light penetrating the beam splitter BS1 is condensed on a detector plane of the imaging device in the anterior eye segment photographing camera 123 by means of the imaging lens 124. The detector plane of the imaging device is arranged at the pupil conjugate position (anterior eye segment conjugate position) Q or in the vicinity of the position. The image sensor is formed of, for example, an area sensor such as a CCD image sensor or a CMOS image sensor. The result of the detection of the return light from the anterior eye segment of the subject's eye E obtained by the imaging device is used for forming an image of the anterior eye segment.

(SLO Optical System)

The optical path of the SLO optical system 130 and the optical path of the OCT optical system 140 are combined by a dichroic mirror DM2. At least part of the SLO optical system 130 is formed as a telecentric optical system. Similarly, at least part of the OCT optical system 140 is formed as a telecentric optical system. The dichroic mirror DM2 combines an optical path formed by the telecentric optical system of the SLO optical system 130 and an optical path formed by the telecentric optical system of the OCT optical system 140. Thereby, an aberration of a pupil (e.g., an exit pupil by the objective lens system 110) becomes small even if the focus position of the optical system 100 is changed by moving the objective lens system 110. Therefore, it becomes easy to adjust a focus state.

Preferably, the dichroic mirrors DM1A (DM1B) and DM2 are disposed in the optical axis O with the relationship of torsion kept. The dichroic mirror DM1A (DM1B) includes a first optical surface. The first optical surface reflects one of at least part of light guided through both of the optical path of the SLO optical system 130 and the optical path of the OCT optical system 140 (the optical path of the optical system 100) and at least part of light guided through the optical path of the anterior eye segment photographing system 120. Further, the first optical surface transmits the other of the at least part of light guided through both of the optical path of the SLO optical system 130 and the optical path of the OCT optical system 140 (the optical path of the optical system 100) and the at least part of light guided through the optical path of the anterior eye segment photographing system 120. The dichroic mirror DM2 includes a second optical surface. The second optical surface reflects one of at least part of light guided through the optical path of the SLO optical system 130 and at least part of light guided through the optical path of the OCT optical system 140. The second optical surface transmits the other of the at least part of light guided through the optical path of the SLO optical system 130 and the at least part of light guided through the optical path of the OCT optical system 140. The dichroic mirrors DM1A (DM1B) and DM2 are disposed such that a plane, which includes a normal line of the first optical surface and an optical axis of the SLO optical system 130, and a plane, which includes a normal line of the second optical surface and the optical axis of the SLO optical system 130, are perpendicular each other or substantially perpendicular each other. In the high magnification photographing mode shown in FIG. 3, the concave lens 113A is not disposed between the dichroic mirror DM1B and the dichroic mirror DM2. Thereby, this eliminates or extremely reduces the astigmatism by means of the dichroic mirror DM1B and the dichroic mirror DM2. As a result, the degradation in image quality can be suppressed. On the other hand, in the wide-angle photographing mode shown in FIG. 3, the image roughness can be allowed more than in the high magnification photographing mode. As a result, the impact on image quality arising from the remaining of the astigmatism becomes small.

The SLO optical system 130 includes an SLO light source 131, a collimator lens 132, a beam splitter BS2, a condenser lens 133, a confocal diaphragm 134, a detector 135, an optical scanner 136, and a lens 137. The beam splitter BS2 is an optical-path combining member to combine an optical path of the return light of the SLO light projected onto the subject's eye E and an optical path of the SLO light.

The SLO light source 131 emits light having a center wavelength of 840 nm, for example. Examples of the SLO light source 131 include a laser diode (LD), a super-luminescent diode (SLD), a laser-driven light source (LDLS), or the like. The SLO light source 131 is arranged at a position (the eye fundus conjugate position) P optically conjugate with the eye fundus (retina) or in the vicinity of the position.

Light emitted from the SLO light source 131 is collimated into a parallel light flux by a collimator lens 132. The light collimated into the parallel light flux penetrates the beam splitter BS2. After penetrating the beam splitter BS2, the light is deflected by the optical scanner 136. The optical scanner 136 is used to scan the eye fundus Ef of the subject's eye E with the light from the SLO light source 131. The optical scanner 136 includes an optical scanner 136X configured to deflect the light in the X direction and an optical scanner 136Y configured to deflect the light in the Y direction. The optical scanner 136X is a mirror whose tilt angle is variable. The tilt of the reflecting surface of the mirror is controlled by a controller 200 (described later). The optical scanner 136X is used for, for example, scanning in the horizontal direction in the eye fundus plane. The optical scanner 136Y is located on the subject's eye E side of the optical scanner 136X. The optical scanner 136Y is a mirror whose tilt angle is variable. The tilt of the reflecting surface of the mirror is controlled by the controller 200. The optical scanner 136Y is used for, for example, scanning in the vertical direction in the eye fundus plane, the vertical direction being perpendicular to the horizontal direction. Either one of the optical scanner 136X and the optical scanner 136Y may be a low-speed scanner such as a galvano mirror, or the like and the other may be a high-speed scanner such as a resonant mirror, a polygon mirror, a microelectromechanical systems (MEMS) mirror, or the like. The reflecting surface of the optical scanner 136Y is arranged at a position (the pupil conjugate position) Q optically conjugate with the pupil of the subject's eye E or in the vicinity of the position. The lens 137 and the dichroic mirror DM2 are located on the subject's eye E side of the optical scanner 136Y. The light from the SLO light source 131 deflected by the optical scanner 136 penetrates the lens 137 and the dichroic mirror DM2, and is projected onto the subject's eye E via the objective lens system 110.

The return light of the light from the SLO light source 131 projected onto the subject's eye E travels through the same optical path, and is reflected toward the detector 135 by the beam splitter BS2. The condenser lens 133 and the confocal diaphragm 134 are arranged between the beam splitter BS2 and the detector 135. The condenser lens 133 condenses the light reflected by the beam splitter BS2. The light condensed by the condenser lens 133 passes through an opening formed in the confocal diaphragm 134 and the light passing through the opening enters a detector plane of the detector 135. The opening formed in the confocal diaphragm 134 is arranged at a position (the eye fundus conjugate position) P optically conjugate with the eye fundus (retina) or in the vicinity of the position. The detector 135 is made of, for example, an avalanche photodiode (APD) or a photomultiplier tube (PMT).

(OCT Optical System)

OCT optical system 140 includes a focusing lens 141, an optical scanner 142, a collimator lens 143, and an interference optical system 150. The interference optical system 150 includes an OCT light source 151, a fiber coupler 152, a fiber coupler 153, a prism 154, and a detector 155.

The focusing lens 141 is movable along an optical axis (an optical path) of the OCT optical system 140 by means of a moving mechanism (not illustrated, a moving mechanism 141D to be hereinafter described). Thereby, a focus position of the OCT optical system 140 can be changed independently of the SLO optical system 130. Therefore, it is possible to finely adjust a focus state of the OCT optical system 140 by moving the focusing lens 141 after adjusting a focus state of the SLO optical system 130 and the OCT optical system 140 by moving the objective lens system 110, for example.

The optical scanner 142 is used to scan the eye fundus Ef of the subject's eye E with a measurement light base on light from the OCT light source 151. The optical scanner 142 includes an optical scanner 142X configured to deflect the light in the X direction and an optical scanner 142Y configured to deflect the light in the Y direction. The optical scanner 142X is a mirror whose tilt angle is variable. The tilt of the reflecting surface of the mirror is controlled by a controller 200. The optical scanner 142X is used for, for example, scanning in the horizontal direction in the eye fundus plane. The optical scanner 142Y is located on the subject's eye E side of the optical scanner 142X. The optical scanner 142Y is a mirror whose tilt angle is variable. The tilt of the reflecting surface of the mirror is controlled by the controller 200. The optical scanner 142Y is used for, for example, scanning in the vertical direction in the eye fundus plane, the vertical direction being perpendicular to the horizontal direction. Either one of the optical scanner 142X and the optical scanner 142Y may be a low-speed scanner such as a low-speed galvano mirror, or the like and the other may be a high-speed scanner such as a high-speed galvano mirror, or the like. The intermediate position between the optical scanner 142X and the optical scanner 142Y is arranged at a position (the pupil conjugate position) Q optically conjugate with the pupil of the subject's eye E or in the vicinity of the position. The collimator lens 143 is located on the OCT light source 151 side of the optical scanner 142Y.

An optical system for acquiring OCT images of the subject's eye E is provided in the interference optical system 150. This optical system has the same configuration as with the conventional swept source OCT apparatus. More specifically, this optical system is an interference optical system that splits the light from the wavelength tunable type (wavelength scanning type) light source into the measurement light and a reference light, makes the measurement light returning from the subject's eye E and the reference light having traveled through a reference optical path interfere with each other to generate interference light, and to detect the interference light. The detection result (detection signal) of the interference light obtained by the interference optical system is a signal representing the spectrum of the interference light. Incidentally, the interference optical system 150 is not configured according to swept-source OCT, but may be configured according to a conventional spectral-domain OCT.

The OCT light source 151 is a wavelength tunable type (i.e., a wavelength scanning type) light source capable of sweeping (scanning) the wavelengths of the OCT light (emitted light). A laser light source including a resonator and emitting light having a center wavelength of 1050 nm, for example, is used as the wavelength tunable type light source. The OCT light source 151 temporally changes the output wavelength in the near infrared wavelength band which cannot be visually recognized by the human eye.

Light L0 output from the OCT light source 151 is guided by an optical fiber f1 to a fiber coupler 152, and divided into the measurement light LS and the reference light LR.

The reference light LR is guided to a fiber emitting end c1 by an optical fiber f2, and a collimator lens 156 is irradiated with the reference light LR emitted from the fiber emitting end c1. The reference light LR emitted from the fiber emitting end c1 is collimated into a parallel light flux by the collimator lens 156. The reference light LR, which has become a parallel light flux, is guided to the prism 154. The prism 154 changes the traveling direction of the reference light LR that has been made into the parallel light flux by the collimator lens 156 in the opposite direction. The optical path of the reference light LR incident on the prism 154 and the optical path of the reference light LR emitted from the prism 154 are parallel. The prism 154 is movable in a direction along the incident light path and the emitting light path of the reference light LR by means of a moving mechanism (not illustrated, a moving mechanism 154D to be hereinafter described). In this case, the moving mechanism is provided with an actuator that generates a driving force for moving the moving mechanism, and a transmission mechanism that transmits the driving force from the actuator to the moving mechanism. The actuator may be a pulse motor. The transmission mechanism may include a combination of gears, and a rack and pinion. As a result, the length of the optical path of the reference light LR is changed.

The reference light LR that has traveled through the prism 154 is converted from the parallel light flux to the convergent light beam by a collimator lens 157 and enters a fiber entrance end c2 of an optical fiber f3, and is guided to a fiber coupler 153 by (through) the optical fiber f3. Incidentally, an optical path length correction member or a dispersion compensation member is arranged between the collimator lens 156 or 157 and the prism 154. The optical path length correction member functions as a delaying means for matching the optical path length (i.e., optical distance) of the reference light LR with the optical path length of the measurement light LS. The dispersion compensation member functions as a dispersion compensation means for matching the dispersion characteristics between the reference light LR and the measurement light LS.

On the other hand, the measurement light LS generated by the fiber coupler 152 is guided to a fiber end c3 by an optical fiber f4. The collimator lens 143 is irradiated with the measurement light LS guided to the fiber end c3. The measurement light LS emitted from the fiber end c3 is collimated into a parallel light flux by the collimator lens 143. The measurement light LS collimated into a parallel light flux reaches the dichroic mirror DM2 via the optical scanner 142 and the focusing lens 141. The measurement light LS is reflected by the dichroic mirror DM2, refracted by the objective lens system 110, and the subject's eye E is irradiated with the measurement light LS. The measurement light LS is scattered (and reflected) at various depth positions of the subject's eye E. The return light of the measurement light LS including such backscattered light advances through the same path as the outward path in the opposite direction and is led to the fiber coupler 152, and then reaches the fiber coupler 153 through an optical fiber f5.

The fiber coupler 153 generates the interference light by superposing the measurement light LS incident through the optical fiber f5 and the reference light LR incident through the optical fiber f3 with each other (i.e., by making the measurement light LS incident through the optical fiber f5 and the reference light LR incident through the optical fiber f3 interfere with each other). The fiber coupler 153 generates a pair of interference lights LC by splitting the interference light generated from the measurement light LS and the reference light LR at a predetermined splitting ratio (for example, 1:1). The pair of interference light LC output from the fiber coupler 153 is guided to the detector 155.

The detector 155 is, for example, a balanced photodiode that includes a pair of photodetectors for respectively detecting the pair of interference lights LC and outputs the difference between the pair of detection results obtained by the pair of photodetectors. The detector 155 sends the detection result (detection signal) to an unillustrated data acquisition system (DAQ). The DAQ is fed with a clock from the OCT light source 151. The clock is generated in the OCT light source 151 in synchronization with the output timing of each wavelength sweeping (i.e., wavelength scanning) within a predetermined wavelength range performed by the wavelength tunable type light source. The DAQ performs the sampling of the detection result obtained by the detector 155 based on the clock, and sends it to an image forming part described later or the like. The image forming part applies Fourier transform or the like to the spectral distribution based on the detection result obtained by the detector 155, for example, with respect to a series of wavelength scans (for each A-line) to form the reflection intensity profile in each A-line. In addition, the image forming part forms image data by applying imaging processing to the reflection intensity profiles of the respective A lines.

[Processing System]

Figure 4:
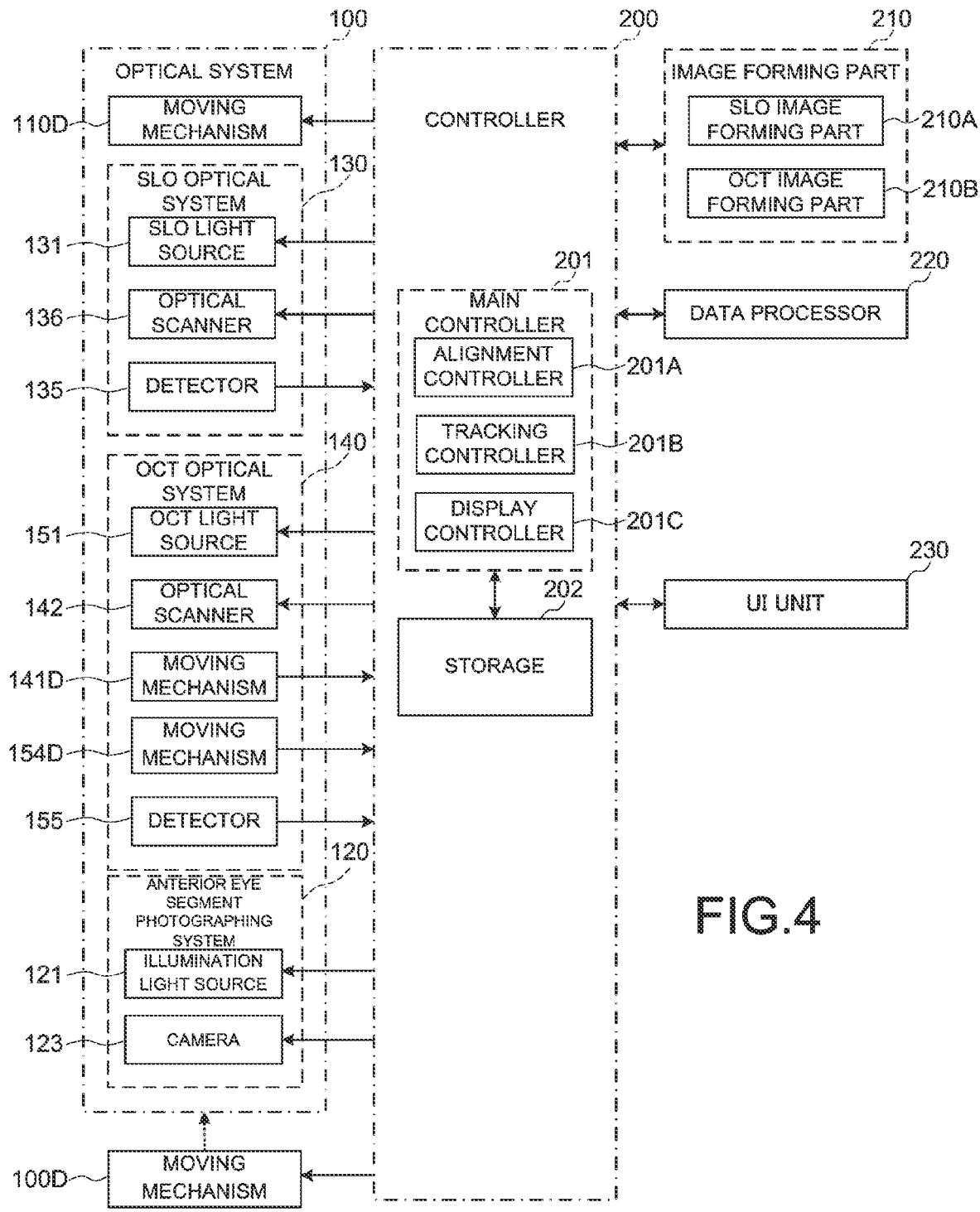
FIG. 4 is a schematic diagram illustrating an example of the configuration of a processing system of the ophthalmic device according to the embodiments.

FIG. 4 illustrates an example of the configuration of a processing system of the ophthalmic device according to the embodiments. In FIG. 4, like reference numerals designate like parts as in FIGS. 1 and 3. The same description may not be repeated.

(Controller)

The controller 200 is the center of the processing system of the ophthalmic device of the embodiments. The controller 200 controls each part of the ophthalmic device. The controller 200 includes a main controller 201 and a storage 202. The functions of the main controller 201 is implemented by a microprocessor, for example. The storage 202 stores, in advance, a computer program for controlling the ophthalmic device. The computer program includes, for example, various light source control programs, optical scanner control program, various detector control programs, image forming program, data processing program, program for user interface, and the like. The microprocessor operates according to the computer programs, and thereby the controller 200 performs the control process.

Examples of the control of the objective lens system 110 include control of the moving mechanism 110D that moves the objective lens system 110 along the optical axis O, and the like. For example, the moving mechanism 110D is provided with an actuator that generates a driving force for moving the moving mechanism 110D and a transmission mechanism that transmits the driving force from the actuator to the moving mechanism 110D. The actuator may be a pulse motor. The transmission mechanism may include a combination of gears, and a rack and pinion. The main controller 201 controls the moving mechanism 110D by sending a control signal to the actuator.

Examples of the control of the SLO optical system 130 include control of the SLO light source 131, control of the optical scanner 136, control of the detector 135, and the like. Examples of the control of the SLO light source 131 include turning on and off the light source, adjustment of amount of light, adjustment of aperture, and the like. Examples of the control of the optical scanner 136 include control of the scanning position and the scanning area by means of the optical scanner 136X, control of the scanning position and the scanning area by means of the optical scanner 136Y, and the like. Examples of the control of the detector 135 include adjustment of exposure of a detecting element, adjustment of gain of a detecting element, adjustment of detecting rate of a detecting element, and the like.

Examples of the control of the OCT optical system 140 include control of the OCT light source 151, control of the optical scanner 142, control of the moving mechanism 141D and the moving mechanism 154D, control of the detector 155, and the like. Examples of the control of the OCT light source 151 include turning on and off of the light source, adjustment of amount of light, adjustment of aperture, and the like. Examples of the control of the optical scanner 142 include control of the scanning position and the scanning area by means of the optical scanner 142X, control of the scanning position and the scanning area by means of the optical scanner 142Y, and the like. The moving mechanism 141D moves the focusing lens 141 along the optical path of the OCT optical system 140. For example, the moving mechanism 141D is provided with an actuator that generates a driving force for moving the moving mechanism 141D and a transmission mechanism that transmits the driving force from the actuator to the moving mechanism 141D. The actuator may be a pulse motor. The transmission mechanism may include a combination of gears, and a rack and pinion. The main controller 201 controls the moving mechanism 141D by sending a control signal to the actuator. The moving mechanism 154D moves the prism 154 in a direction along the incident light path and the emitting light path of the reference light LR. For example, the moving mechanism 154D is provided with an actuator that generates a driving force for moving the moving mechanism 154D and a transmission mechanism that transmits the driving force from the actuator to the moving mechanism 154D. The actuator may be a pulse motor. The transmission mechanism may include a combination of gears, and a rack and pinion. The main controller 201 controls the moving mechanism 154D by sending a control signal to the actuator. Examples of the control of the detector 155 include adjustment of exposure of a detecting element, adjustment of gain of a detecting element, adjustment of detecting rate of a detecting element, and the like.

Examples of the control of the anterior eye segment photographing system 120 include control of the anterior eye segment illumination light source 121, control of the anterior eye segment photographing camera 123, and the like. Examples of the control of the anterior eye segment illumination light source 121 include turning on and off of the light source, adjustment of amount of light, adjustment of aperture, and the like. The control of the anterior eye segment photographing camera 123 includes adjustment of exposure of the imaging devices, adjustment of gain of the imaging devices, adjustment of photographing rate of the imaging devices, and the like.

Examples of the control of the optical system 100 (including the dichroic mirrors DM1A, DM1B and the anterior eye segment photographing system 120) include control of the moving mechanism 100D that moves the optical system 100 in the X direction, the Y direction, and the Z direction, and the like. For example, the moving mechanism 100D is provided with an actuator that generates a driving force for moving the moving mechanism 100D and a transmission mechanism that transmits the driving force from the actuator to the moving mechanism 100D. The actuator may be a pulse motor. The transmission mechanism may include a combination of gears, and a rack and pinion. The main controller 201 controls the moving mechanism 100D by sending a control signal to the actuator.

The main controller 201 includes an alignment controller 201A, a tracking controller 201B, and a display controller 201C.

The alignment controller 201A controls the perform of the alignment for position matching of the optical system 100 with respect to the subject's eye E. The alignment controller 201A controls the moving mechanisms 100D and 110D based on an anterior eye segment image of the subject's eye E obtained by the anterior eye segment photographing system 120. For example, the alignment controller 201A specifies a characteristic site of the anterior eye segment image obtained by the anterior eye segment system 120, and obtains an amount of moving of the moving mechanism 100D etc. so as to cancel an amount of displacement between the position of the specified characteristic site and the predetermined target position. The alignment controller 201A controls the moving mechanism 100D based on the obtained amount of moving, thereby performing the position matching of the optical system 100 with respect to the subject's eye E (in the X direction and the Y direction). The target position may be the predetermined position, or the target position may be the position in the anterior eye segment image designated using the UI unit 230.

For example, the alignment controller 201A can specify a focus state (degree of defocusing) of the anterior eye segment image of the subject's eye E acquired by the anterior eye segment photographing system 120, and obtain an amount of moving of the objective lens system 110 in the Z direction so that the specified focus state becomes a desired focus state. The alignment controller 201A controls the moving mechanisms 100D and 110D based on the obtained amount of moving, thereby performing the position matching of the optical system 100 and the objective lens system 110 with respect to the subject's eye E (in the Z direction). Incidentally, the alignment controller 201A may specify a focus state three-dimensionally based on two or more images having parallax acquired by two or more photographing cameras that photograph the anterior eye segment at different directions from each other, and obtain an amount of moving of the objective lens system 110 in the Z direction so that the specified focus state becomes the desired focus state.

The alignment controller 201A may control the moving mechanism 110D based on the SLO image acquired by the SLO optical system 130, thereby performing the position matching of the objective lens system 110 with respect to the subject's eye E (in the Z direction). In this case, the alignment controller 201A specifies a focus state (degree of defocusing) of the acquired SLO image, and obtains an amount of moving of the objective lens system 110 in the Z direction so that the specified focus state becomes the desired focus state. The alignment controller 201A controls the moving mechanism 110D based on the obtained the amount of moving.

The tracking controller 201B controls the perform of the tracking for the SLO image of the subject's eye E obtained by the SLO optical system 130. For example, the tracking controller 201B specifies a characteristic site of the SLO image at a predetermined timing, and when a position of the specified site is changed, the tracking controller 201B obtains an amount of moving so as to cancel an amount of displacement of the position. The tracking controller 201B controls the perform of the tracking for the SLO image based on the obtained the amount of moving.

Moreover, the tracking controller 201B controls the perform of the tracking for the OCT image of the subject's eye E based on the SLO image, the OCT image being obtained by the OCT optical system 140. For example, the tracking controller 201B specifies a characteristic site of the SLO image at a predetermined timing, and when a position of the specified site is changed, the tracking controller 201B obtains an amount of moving so as to cancel an amount of displacement of the position. The tracking controller 201B controls the perform of the tracking for the OCT image based on the obtained amount of moving. The data processor 220 may be provided with the tracking controller 201B.

The display controller 201C displays various kinds of information on the UI unit 230 described later. Examples of the information displayed on the UI unit 230 include information generated by the controller 200, an image formed by the image forming part 210, information after data processing of the data processor 220, and the like.

(Image Forming Part)

The image forming part 210 includes an SLO image forming part 210A and an OCT image forming part 210B. The SLO image forming part 210A forms image data of the SLO image based on the detection signal received from the detector 135 and a pixel position signal received from the controller 200. The OCT image forming part 210B forms image data of the OCT image (the tomographic image of the eye fundus Ef) based on the detection signal received from the detector 155 and a pixel position signal received from the controller 200. Moreover, the image forming part 210 forms the anterior eye segment image based on the detection result of the reflection light from the anterior eye segment of the subject's eye E obtained by the imaging device of the anterior eye segment photographing camera 123. The various images (the image data) generated by the image forming part 210 are stored in the storage 202, for example.

(Data Processor)

A data processor 220 performs various types of data processing. As the data processing, for example, the data processor 220 performs processing on image data formed by the image forming part 210 or another device. Examples of the processing include various types of image processing, analyzing processing of image, and diagnosis support processing such as image evaluation based on the image data.

(UI Unit)

The UI (User Interface) unit 230 has a function for interchanging information between the user and the ophthalmic device. The UI unit 230 includes a display device and an operation device (input device). The display device may include a display part, and it may include another display device. The operation device includes various hardware keys and/or software keys. In response to the operation contents for the operation device, the controller 200 can output a control signal corresponding to the operation contents to each part of the ophthalmic device. At least part of the display device and at least part of the operation device may be configured integrally. One example of this is the touch panel display.

The objective lens system, in which the objective lens unit 110A is disposed in the optical axis O, is an example of the "first objective lens system" according to the embodiments. The SLO light source 131, the collimator lens 132, the beam splitter BS2, the optical scanner 136, and the lens 137 are one example of the "projection system" or the "SLO projection system" according to the embodiments. The detector 135, the confocal diaphragm 134, the condenser lens 133, the beam splitter BS2, the optical scanner 136, and the lens 137 are one example of the "light receiving system" or the "SLO light receiving system" according to the embodiments. The dichroic mirror DM1A or DM1B is one example of the "first optical-path combining member" according to the embodiments. The OCT light source 151, the fiber coupler 152, the collimator lens 143, the optical scanner 142, and the focusing lens 141 are one example of the "projection system" or the "OCT projection system" according to the embodiments. The detector 155, the fiber couplers 152 and 153, the prism 154, the optical scanner 142, and the focusing lens 141 are one example of the "light receiving system" or the "OCT light receiving system" according to the embodiments. The dichroic mirror DM2 is one example of the "second optical-path combining member" according to the embodiments. The objective lens system, in which the objective lens unit 110B is disposed in the optical axis O, is an example of the "second objective lens system" according to the embodiments.

[Operation]

The operation of the ophthalmic device according to the embodiments will be described.

Figure 5:
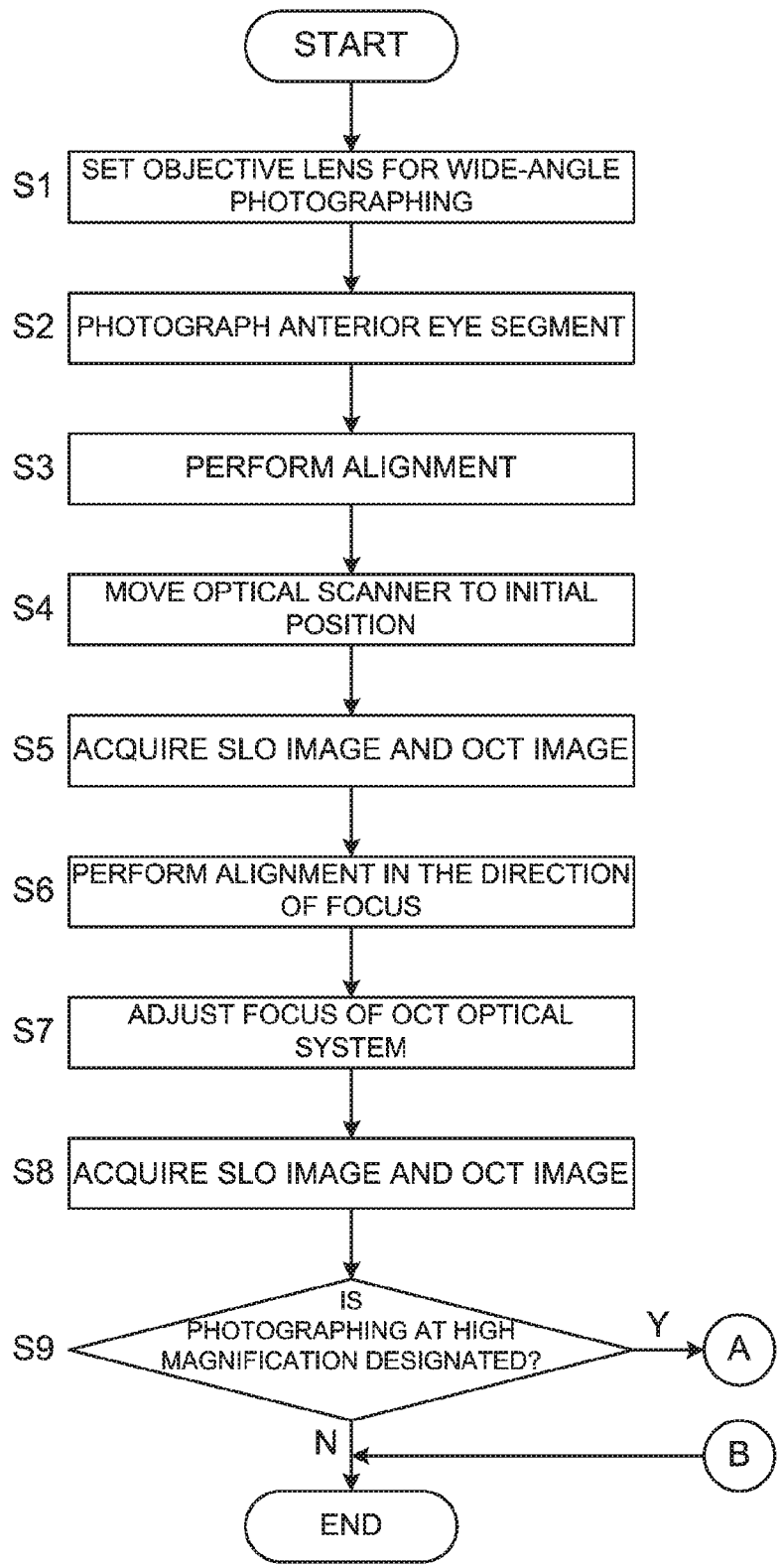
FIG. 5 is a flowchart illustrating an example of the operation of the ophthalmic device according to the embodiments.
Figure 6:
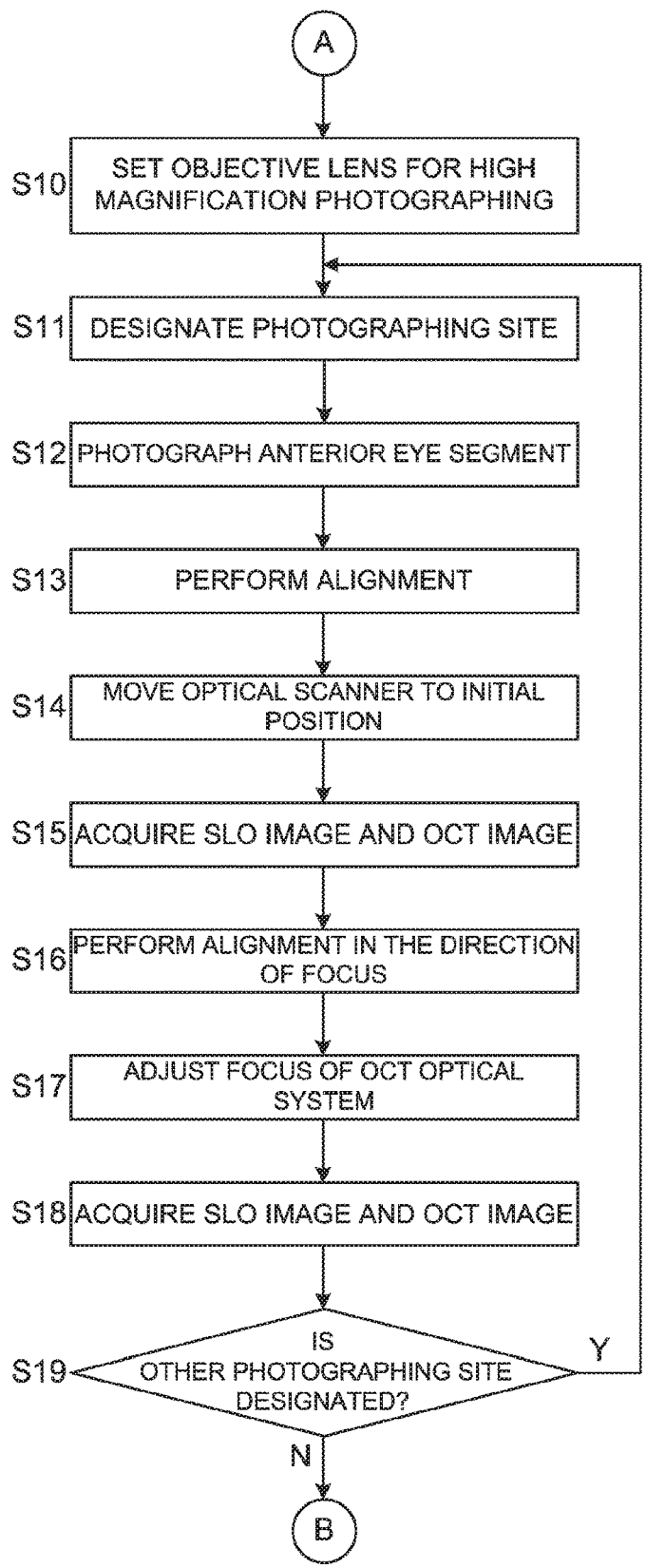
FIG. 6 is a flowchart illustrating an example of the operation of the ophthalmic device according to the embodiments.

FIGS. 5 and 6 illustrate an example of the operation of the ophthalmic device according to the embodiments. FIGS. 5 and 6 represent a flow chart of an operation example of the ophthalmic device according to the embodiments.

(S1)

Firstly, the objective lens unit 110A for the wide-angle photographing mode is set on the optical axis O. For example, a user such as an examiner, a subject, a doctor, or a patient sets the objective lens unit 110A on the optical axis O manually. The operation of the ophthalmic device can proceed to S2 based on an operation for the UI unit 230 by the user. Alternatively, when the type of the objective lens unit is detected and it is determined that the detected type is the pre-registered type corresponding to the wide-angle photographing mode, the operation of the ophthalmic device may proceed to S2.

(S2)

The controller 200 controls the anterior eye segment photographing system 120 to photograph the anterior eye segment of the subject's eye E and to acquire an anterior eye segment image.

(S3)

The alignment controller 201A controls the moving mechanism 100D based on the anterior eye segment image acquired in S2 to perform the position matching of the optical system 100 and the objective lens system 110 with respect to the subject's eye E (in the X direction, the Y direction, and the Z direction).

(S4)

The controller 200 moves the optical scanners 136 and 142 to predetermined initial positions, respectively.

(S5)

The controller 200 turns on the SLO light source 131 and controls the optical scanner 136 to start scanning the eye fundus Ef of the subject's eye E with the light from the SLO light source 131. The SLO image forming part 210A forms an SLO image of the eye fundus Ef based on the detection result of the eye fundus reflection light obtained by the detector 135. Moreover, the controller 200 turns on the OCT light source 151 and controls the optical scanner 142 to start scanning the eye fundus Ef of the subject's eye E with the measurement light LS based on the light emitted from the OCT light source 151. The OCT image forming part 210B forms an OCT image of the eye fundus Ef based on the detection result of the interference light obtained by the detector 155. In S5, the tracking controller 201B may start the tracking control for the SLO image and the tracking control for the OCT image.

(S6)

The alignment controller 201A performs the alignment in the focus direction of the retina based on the anterior eye segment image obtained by the anterior eye segment photographing system 120 or the SLO image obtained in S5. Thereby, it becomes possible to finely adjust the position of the objective lens system 110 in the optical axis O direction.

(S7)

Based on the detection signal of the interference light obtained by the OCT optical system 140, the main controller 201 changes the focus position of the OCT optical system 140. The main controller 201 changes the focus position of the OCT optical system 140, for example, by controlling the moving mechanism 141D so that the amplitude of the detection signal of a predetermined interference light becomes maximum.

(S8)

Once again, by controlling the optical scanner 136, the controller 200 starts scanning the eye fundus Ef of the subject's eye E with the light emitted from the SLO light source 131. The SLO image forming part 210A forms an SLO image of the eye fundus Ef based on the detection result of the eye fundus reflection light obtained by the detector 135. Moreover, once again, by controlling the optical scanner 142, the controller 200 starts scanning the eye fundus Ef of the subject's eye E with the measurement light LS based on the light emitted from the OCT light source 151. The OCT image forming part 210B forms an OCT image of the eye fundus Ef based on the detection result of the interference light obtained by the detector 155. The SLO image and the OCT image obtained in S8 are wide-angle images, respectively.

(S9)

Next, the controller 200 determines whether or not to photograph at the high magnification (whether or not to transit to the high magnification photographing mode). The main controller 201 is capable of detecting the contents of an operation for the UI unit 230. The main controller 201 determines whether or not to photograph at the high magnification, based on the operation contents with respect to the UI unit 230. When it is determined that photographing at the high magnification is to be performed (S9: Y), the operation of the ophthalmic device moves to S10. When it is determined that photographing at the high magnification is not to be performed (S9: N), the ophthalmic device terminates the operation (end).

(S10)

When it is determined that photographing at the high magnification is to be performed (S9: Y), the ophthalmic device waits until the objective lens unit 1108 for the high magnification photographing is set on the optical axis O. For example, the user sets the objective lens unit 1108 on the optical axis O manually. The operation of the ophthalmic device can be moved to S1 based on the operation with respect to the UI unit 230 by the user or be moved to S11 based on the detection result of the type of the objective lens unit disposed in the optical axis O.

(S11)

The main controller 201 receives a designation of the photographing site in the SLO image acquired in S8 by the user using the UI unit 230.

(S12)

The controller 200 controls the anterior eye segment photographing system 120 to acquire anterior eye segment images of the subject's eye E.

(S13)

The alignment controller 201A controls the moving mechanism 100D based on the anterior eye segment images acquired in S12 as described above to perform the position matching of the optical system 100 and the objective lens system 110 with respect to the subject's eye E (in the X direction, the Y direction, and the Z direction).

(S14)

The controller 200 moves the optical scanners 136 and 142 to the initial positions, respectively.

(S15)

The controller 200 starts scanning the eye fundus Ef of the subject's eye E with the light emitted from the SLO light source 131, in the same manner as S5. The SLO image forming part 210A forms an SLO image of the eye fundus Ef based on the detection result of the eye fundus reflection light obtained by the detector 135. Moreover, the controller 200 starts scanning the eye fundus Ef of the subject's eye E with the measurement light LS based on the light emitted from the OCT light source 151. The OCT image forming part 210B forms an OCT image of the eye fundus Ef based on the detection result of the interference light obtained by the detector 155. Also in S15, the tracking controller 201B may start the tracking control for the SLO image and the tracking control for the OCT image, in the same manner as S5.

(S16)

The alignment controller 201A performs alignment in the focus direction of the retina based on the anterior eye segment image obtained by the anterior eye segment photographing system 120 or the SLO image obtained in S15.

(S17)

Based on the detection signal of the interference light obtained by the OCT optical system 140, the main controller 201 changes the focus position of the OCT optical system 140. The main controller 201 changes the focus position of the OCT optical system 140, for example, by controlling the moving mechanism 141D so that the amplitude of the detection signal of a predetermined interference light becomes maximum.

(S18)

Once again, by controlling the optical scanner 136, the main controller 200 starts scanning the eye fundus Ef of the subject's eye E with the light emitted from the SLO light source 131. The SLO image forming part 210A forms an SLO image of the eye fundus Ef based on the detection result of the eye fundus reflection light obtained by the detector 135. Moreover, once again, by controlling the optical scanner 142, the controller 200 starts scanning the eye fundus Ef of the subject's eye E with the measurement light LS based on the light emitted from the OCT light source 151. The OCT image forming part 210B forms an OCT image of the eye fundus Ef based on the detection result of the interference light obtained by the detector 155. The SLO image and the OCT image acquired in S18 are high magnification images, respectively.

Figure 7:
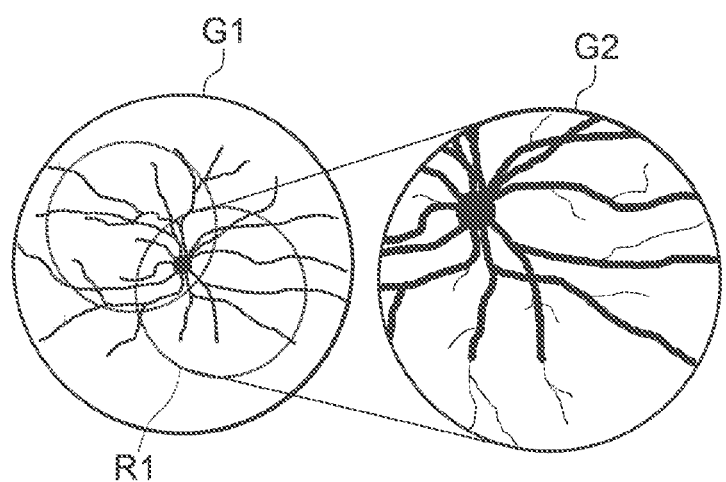
FIG. 7 is an explanatory diagram of the operation of the ophthalmic device according to the embodiments.
Figure 8:
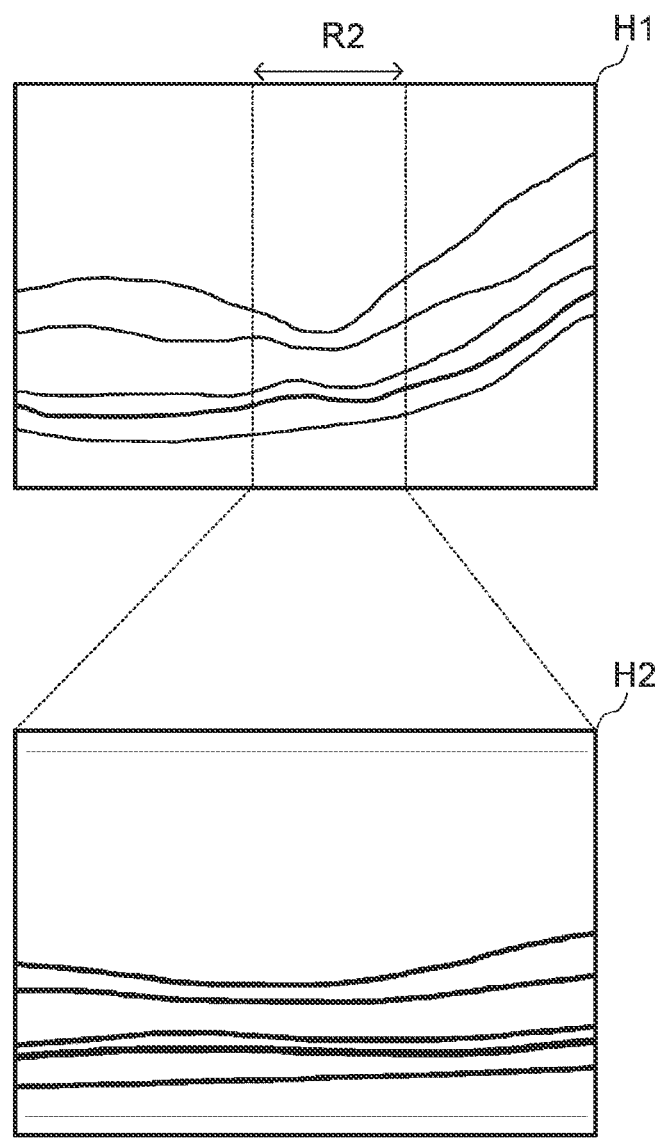
FIG. 8 is an explanatory diagram of the operation of the ophthalmic device according to the embodiments.

As described above, for example, shown in FIG. 7, the high magnification image G2 obtained by imaging photographing site R1 (for example, site in the vicinity of the optic disc) at the high magnification, the photographing site R1 being an attention site in the wide-angle image G1 of the eye fundus acquired in S8, can be obtained. Moreover, for example, shown in FIG. 8, the high magnification tomographic image H2 obtained by imaging photographing site R2 (for example, site in the vicinity of the optic disc) at the high magnification, the photographing site R2 being an attention site in the wide-angle tomographic image H1 of the eye fundus acquired in S8, can be obtained.

(S19)

Next, the controller 200 determines whether or not to perform photographing of the other site. The main controller 201 determines whether or not to perform photographing of the other site, based on the operation contents with respect to the UI unit 230. When it is determined that photographing the other site is to be performed (S19: Y), the operation of the ophthalmic device moves to S11. When it is determined that photographing the other site is not to be performed (S19: N), the ophthalmic device terminates the operation (end).

[Effects]

The effects of the ophthalmic device according to the embodiments are explained.

The ophthalmic device according to the embodiments comprises a first objective lens (the objective lens unit 110A), an optical system (the optical system 100), an anterior eye segment photographing system (the anterior eye segment photographing system 120), and a first optical-path combining member (the dichroic mirror DM1A). The first objective lens system includes two or more lenses (the convex lenses 111A and 112A, the concave lens 113A). The optical system includes a projection system (the SLO projection system and the OCT projection system) configured to project light onto a target eye (the subject's eye E) via the first objective lens system. The anterior eye segment photographing system is used for photographing an anterior eye segment of the target eye. The first optical-path combining member is located between the two or more lenses to combine an optical path of the optical system and an optical path of the anterior eye segment photographing system.

According to such a configuration, the first optical-path combining member is disposed between the two or more lenses included in the first objective lens system. Thereby, this enables to provide an ophthalmic device capable of obtaining an anterior eye segment image, even if light is projected onto the target eye in a wide range. In particular, even when the optical system is moved close to the subject eye so as to irradiate with light over the wide range without increasing the diameter of the objective lens, the alignment can also be performed based on the anterior eye segment image. Thereby, it is possible to provide an ophthalmic device capable easily projecting light in the wide range with respect to subject's eye while downsizing the device. For example, it is possible to observe, photograph the eye fundus etc. of the subject's eye, irradiate the treatment site in the wide range with laser light, or the like.

Further, in the ophthalmic device according to the embodiments, the optical system may comprise a light receiving system (the SLO light receiving system, the OCT light receiving system) receiving return light of the light projected onto the target eye by the projection system via the first objective lens system. The ophthalmic device further may comprise an image forming part (the image forming part 210) configured to form an image based on a light receiving result obtained by the light receiving system.

According to such a configuration, the ophthalmic device is provided with the light receiving system and the image forming part forms an image based on the light receiving result of the light receiving system. Thereby, it is possible to provide an ophthalmic device capable of obtaining easily an image of the eye fundus etc. of the subject's eye in a wide range while downsizing the device.

Further, in the ophthalmic device according to the embodiments, the first objective lens system may be movable along an optical axis of the first objective lens system, and the optical system may comprise an SLO optical system and an OCT optical system. The SLO optical system may include an SLO projection system that projects SLO light from an SLO light source (the SLO light source 131) onto the target eye and an SLO light receiving system that receives return light of the SLO light. The OCT optical system may include an OCT projection system that projects measurement light (the measurement light LS) based on OCT light from an OCT light source (the OCT light source 151) onto the target eye, an OCT light receiving system that receives interference light between return light of the measurement light and reference light based on the OCT light, and a focusing lens (the focusing lens 141) that is disposed in both an optical path of the measurement light and an optical path of the return light of the OCT light and is movable along the optical path of the measurement light and the optical path of the return light of the OCT light. The image forming part may comprise an SLO image forming part (the SLO image forming part 210A) configured to form an SLO image based on a light receiving result obtained by the SLO light receiving system and an OCT image forming part (the OCT image forming part 210B) configured to form an OCT image based on a light receiving result obtained by the OCT light receiving system. The ophthalmic device according to the embodiments further may comprise a second optical-path combining member (the dichroic mirror DM2) coupling an optical path of the SLO optical system with an optical path of the OCT optical system.

According to such a configuration, it is possible to provide an ophthalmic device capable of obtaining easily both of an SLO image and an OCT image of the eye fundus etc. of the subject's eye in a wide range while downsizing the device.

Further, in the ophthalmic device according to the embodiments, the first optical-path combining member may include a first optical surface, the first optical surface reflecting one of at least part of light, which is guided through the optical path of the optical system, and at least part of light, which is guided through the optical path of the anterior eye segment photographing system, and the first optical surface transmitting the other, and the second optical-path combining member may include a second optical surface, the second optical surface reflecting one of at least part of light, which is guided through the optical path of the SLO optical system, and at least part of light, which is guided through the optical path of the OCT optical system, and the second optical surface transmitting the other, and the first optical-path combining member and the second optical-path combining member may be disposed such that a plane including both of a normal line of the first optical surface and an optical axis of the SLO optical system, and a plane including both of normal line of the second optical surface and the optical axis of the SLO optical system are perpendicular each other or substantially perpendicular each other.

According to such a configuration, it is possible to eliminate or extremely reduce the astigmatism by means of the first optical-path combining member and the optical-path combining member. As a result, the degradation in image quality can be suppressed.

Further, in the ophthalmic device according to the embodiments, at least part of the SLO optical system may be formed as a telecentric optical system, and at least part of the OCT optical system may be formed as a telecentric optical system, and the second optical-path combining member may combine an optical path formed by the telecentric optical system in the SLO optical system and an optical path formed by the telecentric optical system in the OCT optical system.

According to such a configuration, an aberration of a pupil (e.g., an exit pupil by the objective lens system) becomes small even if the focus position of the optical system is changed. Therefore, it becomes easy to adjust a focus state.

Further, in the ophthalmic device according to the embodiments, the first objective lens system may be applied to project light in a first range of the target eye, and the ophthalmic device further may comprise a second objective lens system (the objective lens unit 110B) applied in place of the first objective lens system to project light in a second range of the target eye, the second range being narrower than the first range; and a third optical-path combining member (the dichroic mirror DM1B) applied in place of the first optical-path combining member to project light in the second range of the target eye.

According to such a configuration, it is possible to provide an ophthalmic device capable observing the target eye under optical conditions corresponding to projection ranges of light, by switching the objective lens system.

Further, in the ophthalmic device according to the embodiments, the first objective lens system may be applied to project light in a first range of the target eye, and the ophthalmic device further may comprise a second objective lens system (the objective lens unit 110B) applied in place of the first objective lens system to project light in a second range of the target eye, the second range being narrower than the first range and the first optical-path combining member may be shared with when projecting light in the first range and when projecting light in the second range.

According to such a configuration, it is possible to provide an ophthalmic device capable observing the target eye under optical conditions corresponding to projection ranges of light, by switching the objective lens system so that the first optical-path combining member is shared with.

[Modification]

The above-described embodiments are merely an example for carrying out the present invention. Those who intend to implement the present invention can apply any modification, omission, addition, or the like within the scope of the gist of the present invention.

In the embodiments described above, when the operation of the ophthalmic device moves from S9 of FIG. 5 to S10 of FIG. 6, the operation of the ophthalmic device may move to S10 after moving once the objective lens system 110, the optical system 100, or the like in a direction away from the subject's eye after terminating S9.

The controller 200 according to the embodiments may move at least the objective lens system 110 (the optical system 100) so that a working distance in the wide-angle photographing mode becomes shorter than a working distance in the high magnification photographing mode.

In the embodiments described above, examples are described in which the configuration of the optical system 100 has the configuration shown in FIGS. 1 and 3; however, they are not so limited. The optical system according to the embodiments may include an optical system to project a laser light on a treatment site in the eye fundus, an optical system to move a visual target in a state where the subject's eye is being fixated, or the like.

In the embodiments described above, examples are described in which the configuration of the objective lens system 110 has the configuration shown in FIGS. 1 to 3; however, they are not so limited.

The anterior eye segment photographing system according to the embodiments may include two or more cameras for photographing the anterior eye segment of the subject's eye from two or more different directions. In this case, the alignment controller 201A according to the embodiments can perform the alignment in the Z direction from a parallax obtained based on the photographed images from the two or more different directions acquired using these cameras.

In the embodiments described above, examples are described in which the alignment is performed using the anterior eye segment image acquired by the anterior eye segment photographing system 120; however, the acquired anterior eye segment image may be displayed on a display device provided in the UI unit 230. The acquired anterior eye segment image may not be used for the alignment.

What is claimed is:

1. An ophthalmic device comprising:
   a first objective lens system including two or more lenses;
   an optical system including a projection system configured to project light onto a target eye via the first objective lens system, the optical system further comprising:
      an SLO optical system including an SLO projection system that projects SLO light from an SLO light source onto the target eye and an SLO light receiving system that receives return light of the SLO light, wherein at least part of the SLO optical system is formed as a telecentric optical system; and
      an OCT optical system including an OCT projection system that projects measurement light based on OCT light from an OCT light source onto the target eye and an OCT light receiving system that receives interference light between return light of the measurement light and reference light based on the OCT light, wherein at least part of the OCT optical system is formed as a telecentric optical system;
   an anterior eye segment photographing system for photographing an anterior eye segment of the target eye; and
   a first optical-path combining member located between the two or more lenses to combine an optical path of the optical system and an optical path of the anterior eye segment photographing system.

2. The ophthalmic device of claim 1, wherein
   the optical system comprises a light receiving system receiving return light of the light projected onto the target eye by the projection system via the first objective lens system, and
   the ophthalmic device further comprises an image forming part configured to form an image based on a light receiving result obtained by the light receiving system.

3. The ophthalmic device of claim 2, wherein
   the first objective lens system is movable along an optical axis of the first objective lens system,
   the optical system comprises:

a focusing lens that is disposed in both an optical path of the measurement light and an optical path of the return light of the OCT light and is movable along the optical path of the measurement light and the optical path of the return light of the OCT light, the image forming part comprises:
an SLO image forming part configured to form an SLO image based on a light receiving result obtained by the SLO light receiving system; and
an OCT image forming part configured to form an OCT image based on a light receiving result obtained by the OCT light receiving system, and
the ophthalmic device further comprises a second optical-path combining member coupling an optical path of the SLO optical system with an optical path of the OCT optical system.

4. The ophthalmic device of claim 3, wherein
the first optical-path combining member includes a first optical surface, the first optical surface reflecting one of at least part of light, which is guided through the optical path of the optical system, and at least part of light, which is guided through the optical path of the anterior eye segment photographing system, and the first optical surface transmitting the other,
the second optical-path combining member includes a second optical surface, the second optical surface reflecting one of at least part of light, which is guided through the optical path of the SLO optical system, and at least part of light, which is guided through the optical path of the OCT optical system, and the second optical surface transmitting the other, and
the first optical-path combining member and the second optical-path combining member are disposed such that a plane including both of a normal line of the first optical surface and an optical axis of the SLO optical system and a plane including both of a normal line of the second optical surface and the optical axis of the SLO optical system are perpendicular each other or substantially perpendicular each other.

5. The ophthalmic device of claim 3, wherein
the second optical-path combining member combines an optical path formed by the telecentric optical system in the SLO optical system and an optical path formed by the telecentric optical system in the OCT optical system.

6. The ophthalmic device of claim 1, wherein
the first objective lens system is applied to project light in a first range of the target eye, and
the ophthalmic device further comprises:
a second objective lens system applied in place of the first objective lens system to project light in a second range of the target eye, the second range being narrower than the first range; and
a third optical-path combining member applied in place of the first optical-path combining member to project light in the second range of the target eye.

7. The ophthalmic device of claim 1, wherein
the first objective lens system is applied to project light in a first range of the target eye,
the ophthalmic device further comprises a second objective lens system applied in place of the first objective lens system to project light in a second range of the target eye, the second range being narrower than the first range, and
the first optical-path combining member is shared with when projecting light in the first range and when projecting light in the second range.

8. The ophthalmic device of claim 4, wherein
the second optical-path combining member combines an optical path formed by the telecentric optical system in the SLO optical system and an optical path formed by the telecentric optical system in the OCT optical system.

9. The ophthalmic device of claim 2, wherein
the first objective lens system is applied to project light in a first range of the target eye, and
the ophthalmic device further comprises:
a second objective lens system applied in place of the first objective lens system to project light in a second range of the target eye, the second range being narrower than the first range; and
a third optical-path combining member applied in place of the first optical-path combining member to project light in the second range of the target eye.

10. The ophthalmic device of claim 3, wherein
the first objective lens system is applied to project light in a first range of the target eye, and
the ophthalmic device further comprises:
a second objective lens system applied in place of the first objective lens system to project light in a second range of the target eye, the second range being narrower than the first range; and
a third optical-path combining member applied in place of the first optical-path combining member to project light in the second range of the target eye.

11. The ophthalmic device of claim 4, wherein
the first objective lens system is applied to project light in a first range of the target eye, and
the ophthalmic device further comprises:
a second objective lens system applied in place of the first objective lens system to project light in a second range of the target eye, the second range being narrower than the first range; and
a third optical-path combining member applied in place of the first optical-path combining member to project light in the second range of the target eye.

12. The ophthalmic device of claim 5, wherein
the first objective lens system is applied to project light in a first range of the target eye, and
the ophthalmic device further comprises:
a second objective lens system applied in place of the first objective lens system to project light in a second range of the target eye, the second range being narrower than the first range; and
a third optical-path combining member applied in place of the first optical-path combining member to project light in the second range of the target eye.

13. The ophthalmic device of claim 2, wherein
the first objective lens system is applied to project light in a first range of the target eye,
the ophthalmic device further comprises a second objective lens system applied in place of the first objective lens system to project light in a second range of the target eye, the second range being narrower than the first range, and
the first optical-path combining member is shared with when projecting light in the first range and when projecting light in the second range.

14. The ophthalmic device of claim 3, wherein
the first objective lens system is applied to project light in a first range of the target eye,
the ophthalmic device further comprises a second objective lens system applied in place of the first objective lens system to project light in a second range of the target eye, the second range being narrower than the first range, and the first optical-path combining member is shared with when projecting light in the first range and when projecting light in the second range.

15. The ophthalmic device of claim 4, wherein the first objective lens system is applied to project light in a first range of the target eye, the ophthalmic device further comprises a second objective lens system applied in place of the first objective lens system to project light in a second range of the target eye, the second range being narrower than the first range, and the first optical-path combining member is shared with when projecting light in the first range and when projecting light in the second range.

16. The ophthalmic device of claim 5, wherein the first objective lens system is applied to project light in a first range of the target eye, the ophthalmic device further comprises a second objective lens system applied in place of the first objective lens system to project light in a second range of the target eye, the second range being narrower than the first range, and the first optical-path combining member is shared with when projecting light in the first range and when projecting light in the second range.

\* \* \* \* \*

UNITED STATES PATENT AND TRADEMARK OFFICE
CERTIFICATE OF CORRECTION

PATENT NO. : 10,932,664 B2
APPLICATION NO. : 16/061724
DATED : March 2, 2021
INVENTOR(S) : Ryoichi Hirose et al.

It is certified that error appears in the above-identified patent and that said Letters Patent is hereby corrected as shown below:

In the Specification

Column 16, Line 3, "ophthalmic device waits until the objective lens unit 1108" should read --ophthalmic device waits until the objective lens unit 110B--

Column 16, Line 5, "For example, the user sets the objective lens unit 1108 on the optical axis O manually." should read --For example, the user sets the objective lens unit 110B on the optical axis O manually.--

Signed and Sealed this
Twenty-second Day of June, 2021

Drew Hirshfeld
*Performing the Functions and Duties of the
Under Secretary of Commerce for Intellectual Property and
Director of the United States Patent and Trademark Office*